United States Patent [19]

Enderlin

[11] Patent Number: 5,207,104
[45] Date of Patent: May 4, 1993

[54] METHOD FOR DETERMINATION OF THE IN SITU COMPRESSIVE STRENGTH OF FORMATIONS PENETRATED BY A WELL BOREHOLE

[75] Inventor: Milton B. Enderlin, Arlington, Tex.

[73] Assignee: Halliburton Logging Services, Inc., Houston, Tex.

[21] Appl. No.: 700,972

[22] Filed: Aug. 6, 1991

Related U.S. Application Data

[62] Division of Ser. No. 609,854, Nov. 7, 1990.

[51] Int. Cl.$^5$ .......................................... G01N 33/24
[52] U.S. Cl. ...................................................... 73/784
[58] Field of Search ................. 73/784, 84, 151, 121, 73/81, 82, 85

[56] References Cited

U.S. PATENT DOCUMENTS

| | | | |
|---|---|---|---|
| 3,872,717 | 3/1975 | Fox | 73/84 |
| 4,745,802 | 5/1988 | Purfurst | 166/264 |
| 5,056,595 | 10/1991 | Desbrandes | 166/264 |

FOREIGN PATENT DOCUMENTS 845425 6/1952 Fed. Rep. of Germany .......... 73/81

Primary Examiner—Robert Raevis
Attorney, Agent, or Firm—William J. Beard

[57] ABSTRACT

A formation test tool is set forth in the present disclosure and has a snorkel on one side and upper and lower diametrically opposite back-up pistons on the opposite side. The back-up pistons are constructed with a back-up plate on the end of the back-up piston encircling and centered around a formation punch. The formation punch has a small diameter and specified length so that, during operation, the punch contacts the sidewall of the well borehole, and pressure is increased thereafter to force the punch into the formation until fracture failure occurs evidenced by a change in hydraulic pressure and a lurching movement of the back-up piston as the punch penetrates the formation. By knowing the diameter of the punch and by observing the hydraulic pressure necessary to obtain failure of the formation at the point of contact with the punch, data can be obtained which is indicative of the compressive strength of the formation.

3 Claims, 2 Drawing Sheets

METHOD FOR DETERMINATION OF THE IN SITU COMPRESSIVE STRENGTH OF FORMATIONS PENETRATED BY A WELL BOREHOLE

This is a divisional of application Ser. No. 07/609,854 filed Nov. 7, 1990.

BACKGROUND OF THE DISCLOSURE

This disclosure is directed to a method and apparatus for determination of the compressive strength of formations which are penetrated by a well borehole. More particularly, it is a method and apparatus for use during open hole drilling procedures, particularly those which involve positioning a formation test tool in the well. This takes advantage of the manner in which a formation test tool is constructed to provide the additional benefit of the test described herein. By way of background, the formation test tool is normally constructed with a snorkel which extends from one side of the formation test tool sonde so that the snorkel is able to penetrate into formations aligned adjacent to the formation tester. Moreover, the formation tester is normally held in location by means of back-up shoes. Thus, the snorkel extends on one side of the tool in response to urging of a hydraulic system within the tool. Above and below the snorkel, there are separate back-up pistons. For instance, one might be two feet above the snorkel and the other back-up shoe is about two feet below the snorkel. The two back-up shoes are included so that they can extend in the opposite direction (diametrically opposite the snorkel) and prop the formation test tool when the snorkel is extended. The back-up shoes and opposing snorkel particularly reduces differential sticking of the sonde against the sidewall of the borehole during operation. When the snorkel is extended, the two back-up shoes shoes are also extended. When the snorkel is retracted, both of the back-up shoes are normally retracted. This assures a desirable sequence of operation where the snorkel is first extended and then retracted while the snorkel obtains the intended data from its operation.

Measurement of the compressive strength of the rock is an important factor. This data along with other information assists in determining whether or not the formation is permeable. This is particularly helpful since the back-up shoes are located on the opposite side of the snorkel, spaced immediately above and below, and are likely to be contacted against the same formation. Thus, if the snorkel is extended into a particular formation, it is helpful to know the compressive strength of that formation. The compressive strength test is performed during routine operation where the snorkel is extended which motion is accompanied by extension of the two back-up shoes on the opposite side of the formation test tool. To this end, the back-up shoes are equipped with a protruding punch and an adjacent back-up plate, both to be described. The punch and back-up plate both engage the wall of the borehole, and hydraulic pressure readings are taken. The instant of rock failure in response to the urging of the punch will be noted by a change in hydraulic pressure. Separate tests can be performed with each of the two back-up shoes. Thus, two separate data are obtained whereby the failure of the rock making up the formation is noted and the compressive strength of the rock in the formation is then determined. A typical operation sequence involves extension of the snorkel after the extension of the two back-up shoes on the opposite side. They are extended until they touch the adjacent formation when they are stopped and held at that position. One of the two is then further extended so that the protruding punch penetrates and breaks the rock whereby a pressure drop is noted in the hydraulic system extending the back-up shoe. The puncture wound formed in the formation causes this drop in pressure. That back-up shoe is then forced further toward the formation so that the back-up plate then contacts the formation and provides a sure footing. The routine is repeated for the other of the two back-up shoes so that both data are obtained.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
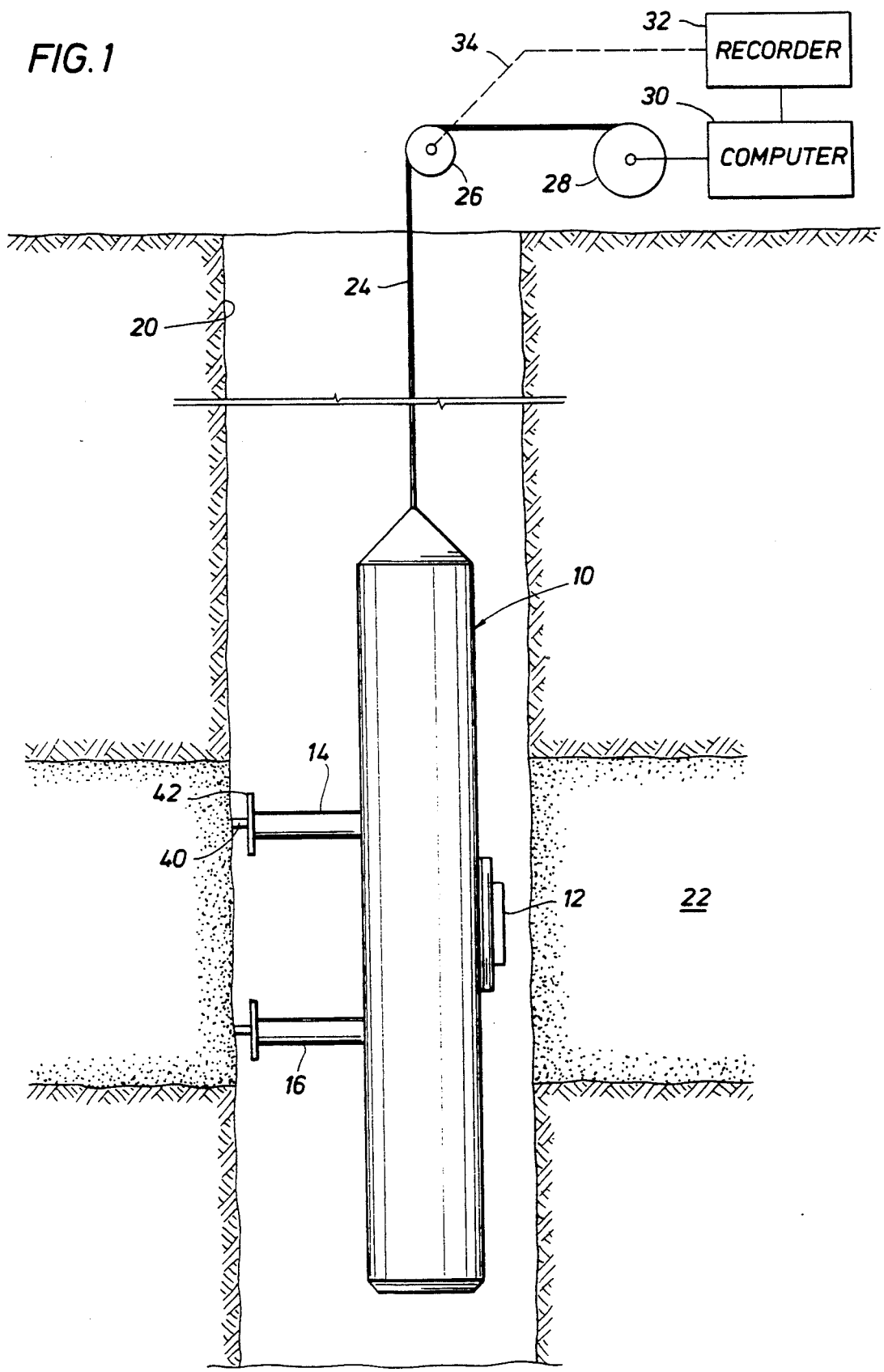
FIG. 1 shows a formation tester suspended in a well borehole for extending a snorkel into a formation wherein back-up shoes are provided on the opposite side of the sonde from the snorkel and the back-up shoes are equipped with a rock punch and back-up plate.

In FIG. 1 of the drawings, the numeral 10 identifies a formation test tool which is constructed in a sonde and which is believed to be well known in the art. It incorporates a snorkel (retracted and hence not shown) which extends outwardly through a contact or facial seal ring 12. This is located on one side of the sonde. On the opposite side of the sonde, there is an upper back-up piston 14 and a similar lower positioned hydraulic powered piston 16. The sonde supports and encloses a tool hydraulic pressure system which provides adequate hydraulic fluid pressure for extension for the snorkel on one side and the back-up pistons 14 and 16 on the opposite side of the sonde. The back-up pistons 14 and 16 are shown extended in this disclosure to emphasize this particular feature. Ordinarily, the back-up pistons are provided with a relatively broad area of contact against the sidewall of the well borehole 20.

The well is shown in open condition. That is, the well has not been cased so that this test data can be obtained from the formations adjacent to the formation test tool 10. A particular formation 22 has been illustrated in a representative fashion in the drawings and is the formation to be tested, and in particular, it is tested for fracture of the rock which makes up the formation. The sonde 10 is supported on an armored logging cable 24 which extends in the well borehole to the surface and passes over a sheave 26 located at the surface. This logging cable is spooled on a large supply reel or drum 28. The data which is obtained through operation of the sonde is provided to a surface located CPU through one or more electrical conductors in the logging cable 24. This data is manipulated in some suitable fashion and is delivered from the CPU 30 to a recorder 32. The data is recorded as a function of depth which is determined by an electrical or mechanical depth measuring system 34. The link between the depth measuring equipment is shown as extending from the sheave 26 to the recorder 32. Thus, the test data for the formation 22 can be obtained and the depth of the formation 22 is indicated at the recorder 32.

The tool hydraulic system provides fluid pressure to extend the back-up pistons 14 and 16. Ordinarily, they are constructed with a relatively broad face contact surface. That is modified for purposes of the present disclosure. This modification contemplates the use of a rock punch 40 which is connected to a back-up plate 42. The rock punch has a specified length up to about one inch. The rock punch has a specified diameter and is made of a relatively tough metal so that it will not bend, break or deflect. The back-up plate 42 is relatively large in diameter compared to the punch 40. Specifically, the punch 40 can have a diameter ranging perhaps to one half inch or so; the preferred diameter being about one quarter inch. The length can vary from about one quarter inch to about three quarters inch. By contrast, the back-up plate can vary from about three quarters to about one or even as much as one and one quarter inches in diameter. The back-up plate preferably fixedly attaches either by threading or otherwise to the back-up piston 14. It provides sufficient contact area so that it anchors against the wall of the borehole 20. The punch, however, is sized so that, on the application of hydraulic pressure through the tool hydraulic system, the punch will puncture and penetrate the formation. Briefly, this occurs in the following fashion. FIG. 1 shows the punch extended the point at which it contacts against the sidewall of the borehole 20. It is shown contacted against the solid formation, ignoring any overlying mud cake which may or may not be formed in the well borehole 20. The punch is then driven by increasing hydraulic pressure. That is, it is forced against the formation 22 with ever increasing hydraulic pressure. If the formation is an unconsolidated sand or the like, it may penetrate rather easily, perhaps even in a linear fashion. If, however, the formation is rock, ordinarily the punch will not penetrate the formation until there is a stress rock fracture. That is, the small circular punch stabbed against the rock which comprises the formation will ultimately punch a hole in the formation, causing the formation to break or fracture in the immediate vicinity of the region where the punch contacts the formation and the rocks will sluff away. This is normally evidenced by an instant drop in hydraulic pressure and is also accompanied by further extension of the back-up shoe; or for a constant pressure system, there will be a sharp rise of hydraulic fluid flow. There will be a small lurch as the punch quickly penetrates into the formation 22, but the lurch is relatively brief and short because the back-up plate 42 then comes into contact with the well borehole. When this occurs, a solid footing is then achieved so that further movement or slippage of the back-up piston is then prevented. If, for instance, the punch has a length of about one half inch, it is not uncommon for the lurching movement to involve approximately one half inch also.

Figure 2:
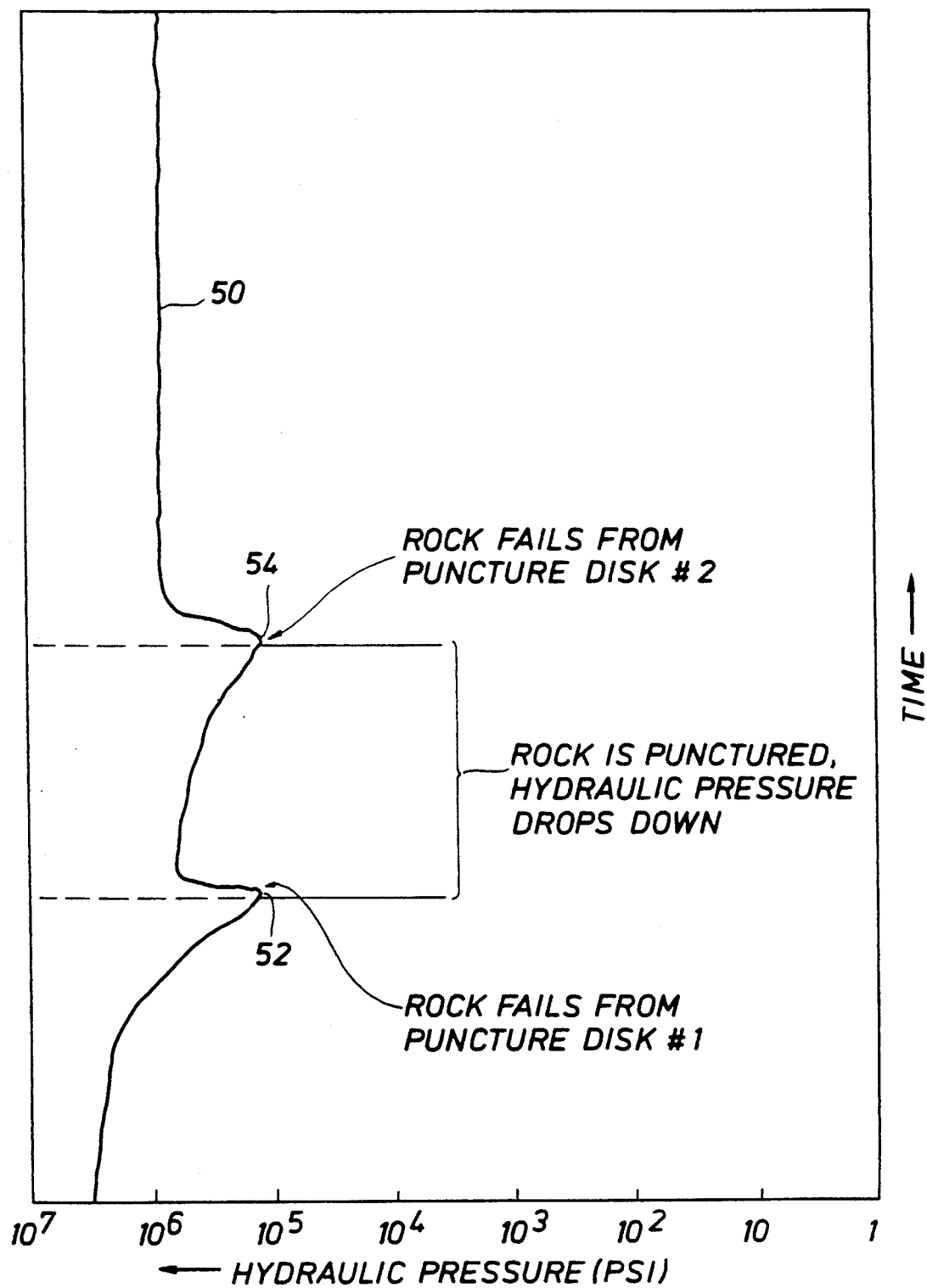
FIG. 2 is a plot of hydraulic pressure versus time showing the change in hydraulic pressure with failure of the rock so that the in situ compressive strength of the rock can be determined.

As stated above for the upper back-up piston, the foregoing is also applicable to the lower back-up piston 16. That is, it punctures and obtains data in the same procedure. Therefore, the two systems operate in similar fashion to obtain data which ought to be the same. They are preferably operated at different moments in time. Thus, a first data is obtained from one back-up piston and a second data is obtained from the other. This is illustrated in FIG. 2 of the drawings. There, the passage of time is indicated in one dimension of the graph while the curve 50 describes the system hydraulic pressure as applied to the respective hydraulic piston and cylinder arrangements used to operate the back-up pistons. The first dip in the curve at 52 is involved with extension of the first back-up piston and the failure of the formation when it breaks in compressive loading. The second peak 54 indicates the second failure and is the second data point resulting from operation of the second back-up piston. As will be understood, hydraulic pressure hits a plateau thereafter, and further increase in the pressure does not provide any more meaningful data. Dependent on scale factors including the diameter of the punch, and also the length of the punch, the compressive strength can then be determined. In other words, the compressive strength at which failure occurs is a function of hydraulic pressure and diameter of the punch. The diameter of the punch is known at the time of installation, and the hydraulic pressure can be monitored during operation. In typical operation, the upper and lower punches can be identical or they may have different diameters. If different, the failure modes will likely occur at different hydraulic pressures, and this is suggested by the curve in FIG. 2 of the drawings where the peaks 52 and 54 occur at different pressures. Determination of the pressures at the instant of failure can be obtained by the type of graph which is shown in FIG. 2. Therefore, determinations can be made of the formation failure mode.

After the two back-up pistons have been extended where they contact the back-up plates on the formation and then are retracted, the sonde can be moved to another location in the well borehole. So long as the punch and back-up plate do not fracture, bend or otherwise become inoperative, the foregoing routine can be repeated time and again. For instance, the sonde can be raised or lowered to obtain data from another elevation in the well. This data can be obtained simultaneously with or independently of data obtained by means of the extended snorkel on the opposite side of the sonde. In fact, the data relating to compressive strength of the formations can be obtained either simultaneous with or independently of any data obtained by means of snorkel operation of the formation tester 10.

While the foregoing is directed to the preferred embodiment, the scope thereof is determined by the claims which follow.

What is claimed is:

1. A hydraulically operated wireline formation tester tool for taking fluid samples in a well borehole and simultaneously measuring the compressive strength of rocks along the well borehole which comprises:

(a) a formation tester having a hydraulically extendible fluid sample taking snorkel;

(b) upper and lower longitudinally spaced back-up pistons located diametrically opposite said snorkel and which are adapted to hydraulically extend from the formation tester toward the sidewall defining a well borehole in which the formation tester is placed; and (c) plural rock penetrating punches, at least one associated with each of said upper and lower back-up pistons and adjacent to shouldered back-up plates supported on said back-up pistons for punching and thereby engaging the formation sidewall, said punches being of generally circular cross section and each having a different diameter.

2. The apparatus of claim 1 further including means for indicating hydraulic pressure within said tester tool at the instant of punch penetration into the formation.

3. The apparatus of claim 2 wherein said back-up plates are circular and have a substantially larger diameter than the larger of said rock penetrating punches.

* * * * *